US007008409B2

(12) United States Patent
Spiezio et al.

(10) Patent No.: US 7,008,409 B2
(45) Date of Patent: Mar. 7, 2006

(54) DISPOSABLE NURSING BREAST PAD WITH MEDICATION

(76) Inventors: Cindy L. Spiezio, 1209 O'Connell Cir., New Lenox, IL (US) 60451; Michael Spiezio, 1209 O'Connell Cir., New Lenox, IL (US) 60451

( * ) Notice: Subject to any disclaimer, the term of this patent is extended or adjusted under 35 U.S.C. 154(b) by 286 days.

(21) Appl. No.: 10/353,323

(22) Filed: Jan. 29, 2003

(65) Prior Publication Data
US 2004/0058619 A1    Mar. 25, 2004

Related U.S. Application Data

(60) Provisional application No. 60/413,187, filed on Sep. 24, 2002.

(51) Int. Cl.
*A61F 13/15* (2006.01)
(52) U.S. Cl. ............... 604/385.07; 604/385.03
(58) Field of Classification Search ........... 604/385.07, 604/385.03, 385.14, 363, 364, 304; 450/36–37, 450/55–57; 602/41–43
See application file for complete search history.

(56) References Cited

U.S. PATENT DOCUMENTS

| | | | | |
|---|---|---|---|---|
| 4,700,699 A | * | 10/1987 | Tollerud et al. ............ 604/358 |
| 5,235,974 A | * | 8/1993 | Miller ........................ 607/108 |
| 5,603,653 A | | 2/1997 | Hartman |
| 5,843,062 A | | 12/1998 | Reidmiller |
| 5,931,717 A | | 8/1999 | Lidji |
| 6,036,577 A | | 3/2000 | Coburn |
| 6,039,629 A | | 3/2000 | Mitchell |
| 6,063,110 A | * | 5/2000 | Stedman ..................... 607/108 |
| 6,390,886 B1 | | 5/2002 | Roberts |
| 6,488,948 B1 | * | 12/2002 | Danieli ........................ 424/404 |
| 6,566,577 B1 | * | 5/2003 | Addison et al. ............. 602/56 |
| 6,756,520 B1 | * | 6/2004 | Krzysik et al. ............. 604/360 |
| 2003/0004485 A1 | | 1/2003 | Leeder |

OTHER PUBLICATIONS

BABYCENTER.com; Disposable Breast Pads by Avent; Jan. 23, 2003.
BABYCENTER.com; Washable Cotton Breast Pads by Medela; Jan. 23, 2003.

* cited by examiner

*Primary Examiner*—Tatyana Zalukaeva
*Assistant Examiner*—C. Lynne Anderson

(57) ABSTRACT

A disposable nursing breast pad is contoured to fit the breast of a nursing woman and is comprised of a soft, highly absorbent material. Disposed adjacent the center of the pad's inner surface is a lubricating moisturizer, such as lanolin, to protect the woman's nipple and prevent dryness and cracking. The pad's outer surface is provided with an adhesive for adhering to the inner surface of clothing, such as a regular or nursing brassiere, for securely maintaining the nursing pad in position on the woman's nipple when not nursing to absorb leaked milk and prevent staining of a garment worn by the woman. The adhesive is preferably in the form of a pair of arcuate adhesive strips respectively disposed above and below the center of the pad and adjacent to the pad's outer periphery.

1 Claim, 3 Drawing Sheets

DISPOSABLE NURSING BREAST PAD WITH MEDICATION

This application claims priority to U.S. Provisional Patent Application No. 60/413,187 filed on Sep. 24, 2002.

FIELD OF THE INVENTION

This invention relates generally to a breast pad for a nursing woman which provides increased comfort and improved wearability when not nursing, and is particularly directed to a disposable nursing breast pad having an inner medicated portion in contact with a nipple for increased comfort and an outer adhesive portion for securely maintaining the pad in position over the woman's breast when not nursing.

BACKGROUND OF THE INVENTION

Nursing or breast pads are commonly used by nursing women to prevent milk, which may leak from the woman's breasts, from staining clothing and bed linens when the woman is not nursing. As such, the breast pad is typically comprised of a multi-layer material having high absorbency and a generally concave shape to snugly fit over the woman's breast, and particularly over the nipple portion of the breast. During nursing, a woman produces a first type of milk generally referred to as hind-type milk for nourishing the child. While initially the rate of milk production is unregulated, eventually the woman's milk production adjusts to the needs of the child. However, the production of a second type of milk, commonly referred to as fore-milk, continues regardless of the time of day and the child's feeding schedule, even in the event that a feeding is missed.

It is this fore-milk, which can give rise to leakage from the nipples, particularly at night. A nursing breast pad positioned over the nipple is intended to absorb leaked milk and prevent staining of garments and bed clothing, hence the high absorptivity of these breast pads. However, the leaked milk which is absorbed by the breast pad has nowhere to go and the wet breast pad remains in contact with the woman's nipple. Disposable nursing breast pads were introduced to at least partially address this problem by facilitating the frequent changing of the breast pad for the woman's comfort. However, occasions frequently arise when it is difficult, if not impossible, for a nursing woman to replace a saturated nursing breast pad with a dry one. One such occasion is at night when the woman is not nursing and is asleep. The longer the nipple remains in contact with the wet nursing breast pad, the more likely the nipple will become dry and cracked and quite sensitive to physical contact. This unfortunate set of circumstances frequently coincides with a highly sensitive condition in the woman's nipples arising from the breast feeding process itself.

It is, of course, highly desirable to maintain the nursing breast pad securely in fixed position over the woman's nipple. Adhesive materials have been applied to the outer surface of the nursing breast pad to engage and adhere to an inner surface of the woman's garment, such as a regular or nursing brassiere. It is particularly difficult to maintain the nursing breast pad in proper position at night during sleep when leakage from the woman is likely to stain the woman's bed clothing and bedding materials such as sheets and covers. Some nursing breast pads currently available make use of an adhesive disposed on an outer surface, but are of limited use because of the location and area of application of the adhesive material on the pad. Current nursing breast pads are easily detached from a woman's garment resulting in movement of the pad from the woman's nipple and/or folding over of the pad on itself so that it no longer engages the nipple resulting in failure of the pad to perform its intended function.

The present invention addresses the aforementioned limitations of prior art disposable nursing breast pads by providing a nursing breast pad having a lubricating moisturizer disposed on its inner surface and in contact with the woman's nipple for soothing and protecting the nipple from becoming dry and cracked making nursing difficult, if not impossible. The inventive disposable nursing pad further includes an adhesive material disposed on its outer surface in a manner which securely attaches the pad to the inner surface of the woman's garment, such as a regular or nursing brassiere, to securely maintain the pad in position over the woman's nipple, even at night while asleep.

OBJECTS AND SUMMARY OF THE INVENTION

Accordingly, it is an object of the present invention to provide a disposable breast pad for a nursing woman which provides increased comfort and improved wearability when not nursing.

It is another object of the present invention to provide continuous conditioning for the nipple of a nursing woman to prevent discomfort caused by dryness and cracking.

A further object of the present invention is to provide a disposable breast pad for wear by a nursing woman which adheres to the inner surface of a worn garment, such as a regular or nursing brassiere, for maintaining the pad securely in fixed position on the woman's nipple.

Yet another object of the present invention is to provide a soft, absorbent pad for wear by a nursing woman which affords continuous lubrication for the woman's entire nipple for soothing, healing and protecting the nipple from dryness and cracking and the accompanying soreness.

This invention contemplates a disposable nursing breast pad for absorbing fluid secreted by a nipple of a woman's breast, the nursing breast pad comprising: an outer layer disposed on the woman's breast and covering her nipple; an inner absorbent layer disposed on an inner portion of the outer layer and positioned in contact with the woman's breast for absorbing fluid secreted by the nipple; and medication disposed in or on said inner layer and in contact with the nipple for lubricating the nipple and preventing it from drying out and cracking.

This invention further contemplates a disposable nursing breast pad for absorbing fluid secreted by a nipple of a woman's breast, the nursing breast pad comprising: an outer layer disposed on the woman's breast and including a central portion covering her nipple; an inner absorbent layer disposed on an inner portion of the outer layer and positioned in contact with the woman's breast for absorbing fluid secreted by the nipple; and an adhesive disposed on the outer layer for attachment to a garment worn by the woman for maintaining the breast pad securely in fixed position on the woman's breast, wherein the adhesive is symmetrically disposed with respect to the central portion of the breast pad to prevent displacement of the breast pad from the woman's breast.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE PREFERRED EMBODIMENTS

Figure 1:
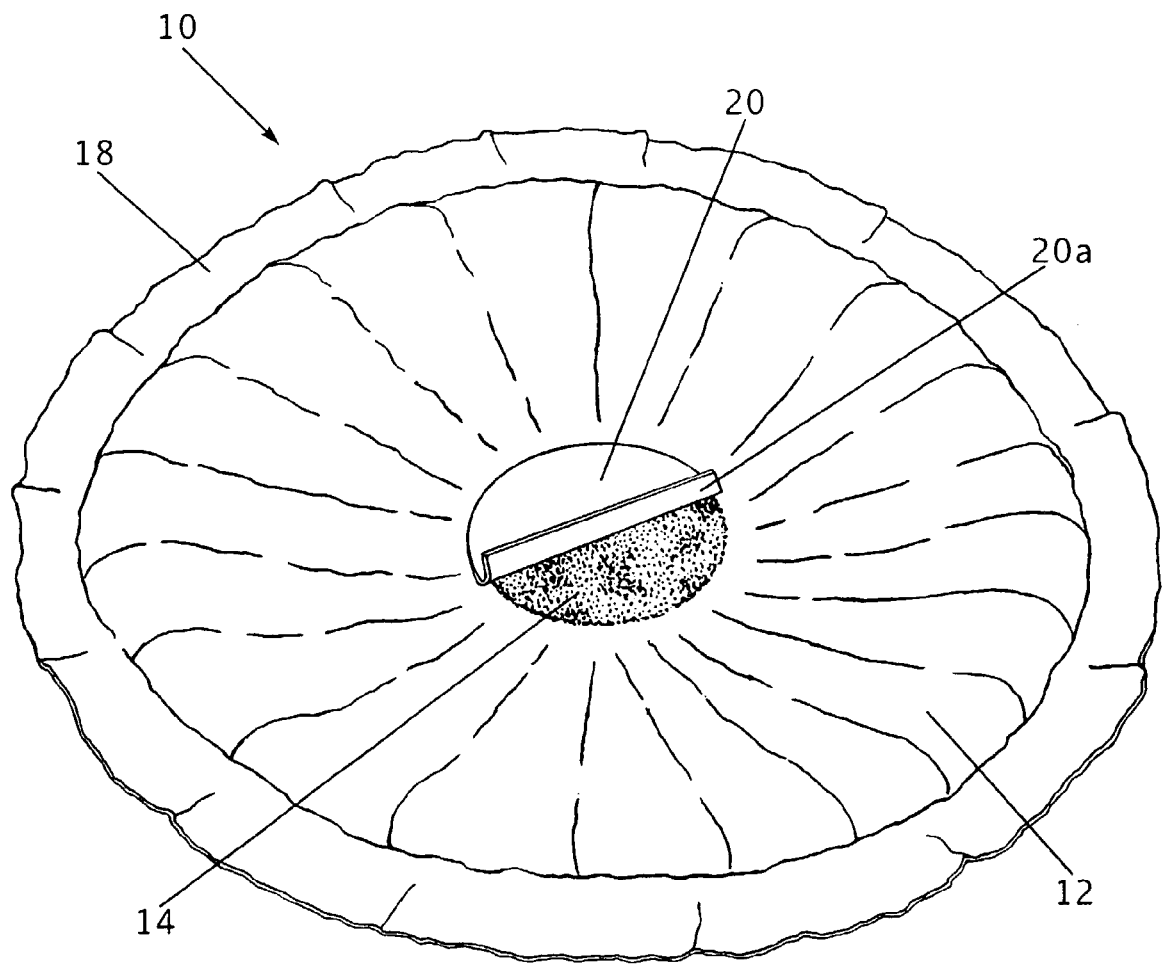
FIG. 1 is a perspective view showing an inner portion of a disposable nursing breast pad in accordance with the present invention which is placed in contact with a woman's breast for absorbing leaked milk while lubricating and soothing the woman's nipple.
Figure 2:
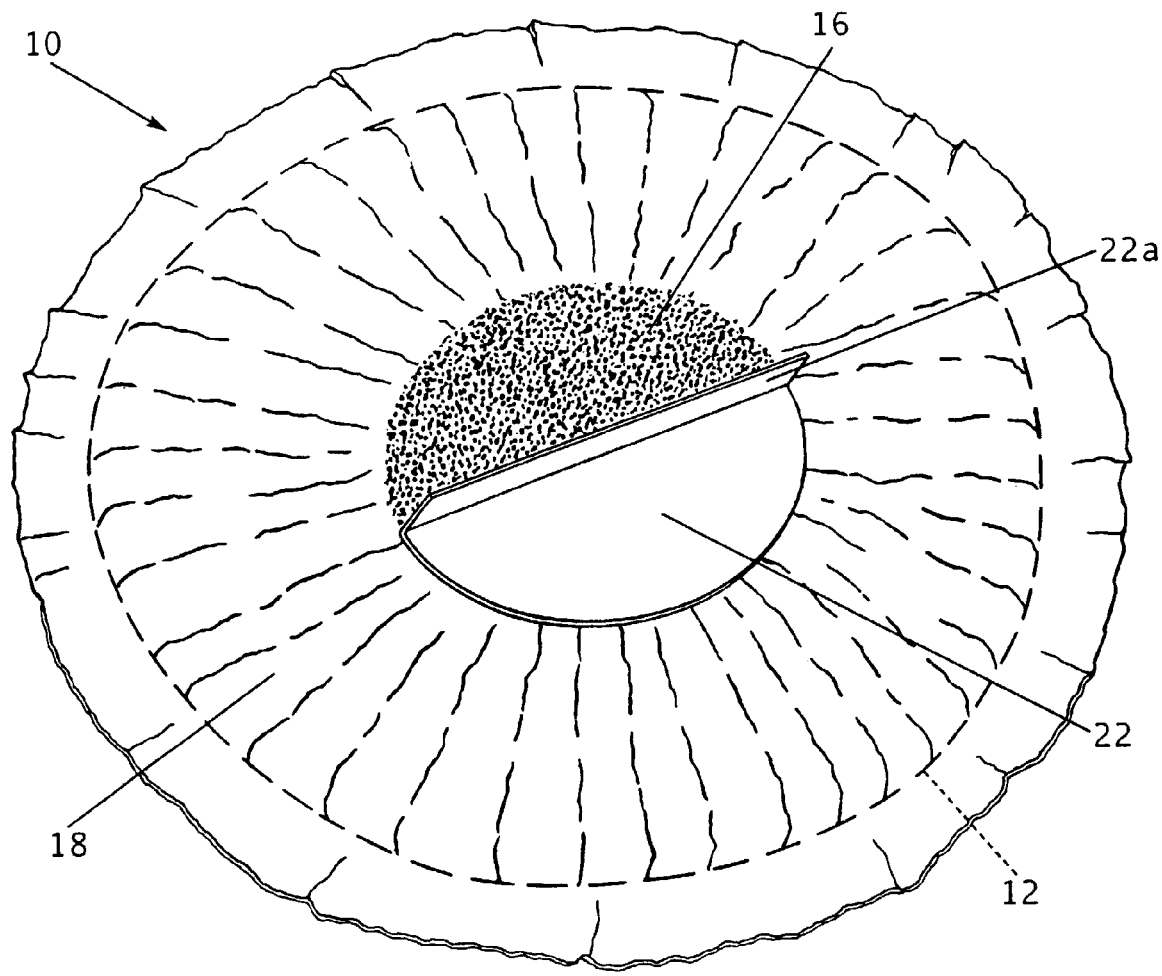
FIG. 2 is a perspective view of an outer portion of the inventive disposable nursing breast pad which includes an adhesive member for maintaining the pad securely in position on a woman's breast.

Referring to FIG. 1, there is shown a perspective view of an inner portion of a disposable nursing breast pad 10 in accordance with the present invention which is placed in contact with a woman's lactating breast for absorbing leaked milk while lubricating and soothing the woman's nipple. FIG. 2 is a perspective view of an outer portion of the inventive disposable nursing breast pad 10 which includes an adhesive member 16 for maintaining the pad securely in position on the woman's breast.

The disposable nursing breast pad 10 is generally circular in shape and is contoured so as to receive and engage the breast of a woman and cover her nipple. Thus, the inner surface of the nursing breast pad 10 as shown in FIG. 1 is generally concave, while its outer surface as shown in FIG. 2 is convex. Nursing breast pad 10 has a multi-layer structure and includes an inner absorbent layer 12 in contact with the woman's breast and an outer layer 18. The inner absorbent layer 12 and the outer layer 18 may be bonded together by conventional means such as by conventional thermal bonding. The inner absorbent layer 12 is preferably comprised of a non-woven fabric material which has a high coefficient of fluid absorbance. One well known fiber material commonly used in these types of applications is comprised of copolymer micro-fibers. The inner absorbent layer 12 may itself include an inner layer in contact with the woman's breast which allows the woman's milk to pass into and be absorbed by the pad's inner absorbent layer 12. The outer layer 18 is preferably comprised of a moisture impermeable material and is disposed against the woman's clothing such as a regular or nursing brassiere (not shown for simplicity). The outer layer 18 may be conventional in composition and structure and preferably is in the form of a web of non-woven fibers preferably treated with a laminating material for rendering the outer layer moisture impermeable so as to prevent the woman's milk from passing through the nursing breast pad 10 and staining the woman's clothes and bedding. An example of a laminating material which could be used for the outer layer 18 of the nursing breast pad 10 is a thin material treated with a light plastic or rubber latex to render the thin layer moisture impermeable. The structure and configuration of the nursing breast pad 10 described thus far is conventional and well-known to those familiar with disposable nursing breast pads.

In accordance with one aspect of the present invention, disposed on the inner surface of the nursing breast pad 10 at or adjacent to its center is a medication 14. Medication 14 is positioned on or within the inner absorbent layer 12 so as to engage and completely cover the woman's nipple. Medication 14 may take on virtually any form provided that it is large enough to fully cover the woman's generally circular-shaped nipple. Medication 14 may be deposited on the inner surface of the inner absorbent layer 12 or may be absorbed into and permeate the center portion of the inner absorbent layer provided that the medication contacts the woman's nipple. The purpose of the inner absorbent layer 12 is to absorb discharged milk and carry it away from the woman's breast. The purpose of medication 14 is to provide continuous lubrication for the woman's nipple to prevent it from drying out, cracking and becoming sore. Medication 14 can be comprised of any conventional medicinal composition used for preventing the drying out of skin such as lanolin or Vaseline®. Disposed over medication 14 is a first covering layer 20. FIG. 1 shows only one half of the first covering layer 20 in position on medication 14, it being understood that the other half of the covering would be placed over the medication to protect it from contact with something prior to placing the nursing breast pad in use on a nursing woman's breast. Adhesive (not shown) is disposed on an inner surface of the first covering layer 20 for affixing the first covering layer 20 in the medication 14. As shown in FIG. 1, the first covering layer 20, which preferably is comprised of paper, may include a gripping tab portion 20a to facilitate its removal from the nursing breast pad 10.

In accordance with another aspect of the present invention, the outer layer 18 of the nursing breast pad 10 is provided with an adhesive 16 as shown in the perspective view of FIG. 2. Adhesive 16 is generally circular in shape and is disposed on and about the center portion of the nursing breast pad 10. Disposed over the adhesive 16 is a second covering layer 22 for protecting the adhesive prior to use. As shown in FIG. 2, one half of the second covering layer is shown as element 22, it being understood that a similarly configured one half covering layer is disposed over the uncovered portion of the adhesive 16 prior to use. The second covering layer 22 protects the adhesive 16 prior to use and maintains it in a tacky condition. The second covering layer 22 is adapted for manual grasping and pulling off of the adhesive 16 as is well known in these types of adhesive items. Covering layer 22 thus may be provided with a tab portion 22a extending upwardly to facilitate grasping and removing the covering layer from adhesive 16. Adhesive 16 is symmetrically disposed about the center portion of the nursing breast pad 10 to provide secure engagement with a garment worn by the nursing woman for securely maintaining the nursing breast pad in position on the woman's breast. By positioning portions of the adhesive 16 above and below as well as to the right and left of the center portion of the nursing breast pad 10, the adhesive provides more secure positioning of the nursing breast pad on the woman's breast than currently available. By symmetrically positioning the adhesive 16 about the center portion of the nursing breast pad 10 and having the adhesive extend outwardly therefrom, the adhesive also prevents folding of the nursing breast pad back upon itself which causes discomfort to the woman and increases the likelihood that discharged milk will bypass the nursing breast pad 10 and contact the woman's clothing.

Figure 3:
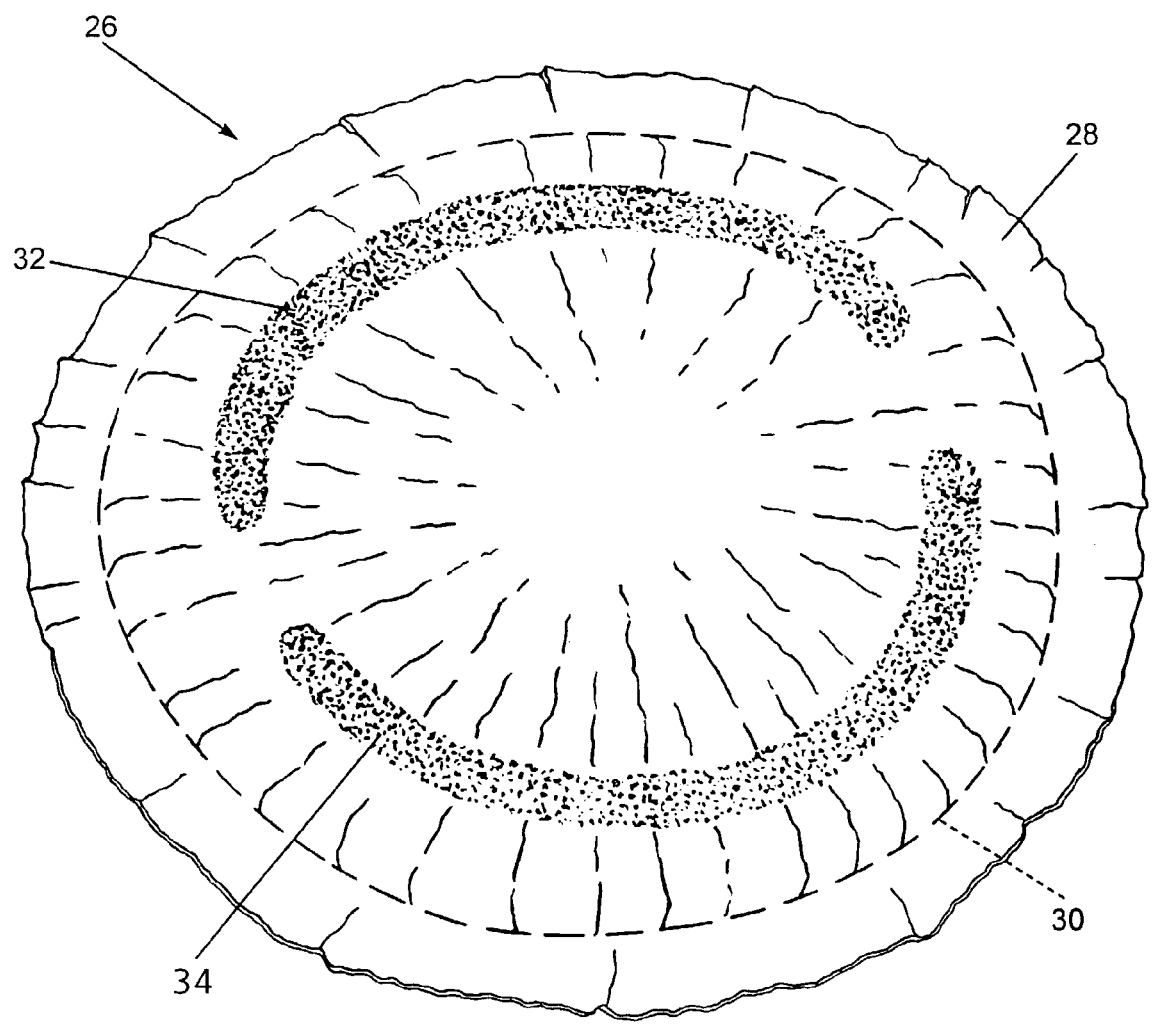
FIG. 3 is a perspective view of the outer portion of another embodiment of a disposable nursing breast pad in accordance with the present invention having a pair of spaced arcuate adhesive members for adhering to a woman's garment for maintaining the pad in fixed position on her breast.

Referring to FIG. 3, there is shown a perspective view of the outer portion of another embodiment of a disposable nursing breast pad 26 in accordance with the present invention. As in the previously described embodiment, the nursing breast pad 26 includes an outer layer 28, an inner layer 30 (shown in dotted line form), and an inner medication which is not shown in the figure for simplicity. The nursing breast pad 26 further includes first and second adhesive strips 32 and 34, each of which has an arcuate shape with its concave surface in facing relation to a center portion of the nursing breast pad. The first and second adhesive strips 32, 34 are further disposed adjacent the peripheral edge of the pad's outer layer 28 which provides improved gripping action of the adhesive strips with the inner surface of a garment of a woman wearing the nursing breast pad 26. This affords more secure and stable positioning of the nursing breast pad 26 on the woman's breast. In addition, the first and second adhesive strips 32, 34 extend substantially around the entire periphery of the nursing breast pad 26 to further enhance the positioning stability of the nursing breast pad on the woman's breast. Each of the first and second adhesive strips 32, 24 is preferably provided with a removable cover as previously described, although this is not shown in FIG. 3 for simplicity.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A disposable nursing breast pad for absorbing fluid secreted by a nipple of a woman's breast, said nursing breast pad comprising:

an outer layer disposed on the woman's breast and covering her nipple;

an inner absorbent layer disposed on an inner portion of said outer layer and positioned in contact with the woman's breast for absorbing fluid secreted by the nipple;

medication disposed in or on the center of said inner absorbent layer and in contact with the nipple for lubricating the nipple and preventing it from drying out and cracking;

a removable covering disposed on said inner absorbent layer or on said medication to protect said medication prior to use of said nursing breast pad, wherein said removable covering includes a gripping tab to facilitate its removal from the nursing breast pad;

first adhesive means disposed on an inner surface of said removable covering for affixing the covering to said medication; and second adhesive means disposed on said outer layer for attachment to a garment worn by the woman for maintaining said nursing breast pad securely in a fixed position on the woman's breast, wherein said second adhesive means includes first and second adhesive strips each having an arcuate shape with the concave surface of said strips in a facing relation to a central portion above and below the center of the breast pad to prevent displacement of said breast pad from the woman's breast.

* * * * *